US006689942B2

(12) United States Patent
van den Bosch et al.

(10) Patent No.: US 6,689,942 B2
(45) Date of Patent: Feb. 10, 2004

(54) INBRED BROCCOLI LINE BRM50-3905

(75) Inventors: Franciscus van den Bosch, Kesteren (NL); Meinardus Petrus Boon, Hoorn (NL)

(73) Assignee: Seminis Vegetable Seeds Inc., Woodland, CA (US)

( * ) Notice: Subject to any disclaimer, the term of this patent is extended or adjusted under 35 U.S.C. 154(b) by 0 days.

(21) Appl. No.: 09/845,672

(22) Filed: Apr. 30, 2001

(65) Prior Publication Data

US 2002/0188967 A1 Dec. 12, 2002

(51) Int. Cl.[7] .............................. A01H 1/02; A01H 5/00; A01H 5/10; C12N 5/04; C12N 15/82
(52) U.S. Cl. ..................... 800/306; 800/260; 800/278; 800/303; 435/410; 435/421; 435/430.1
(58) Field of Search ......................... 435/4, 410, 419, 435/421, 430.1; 800/260, 264, 265, 266, 267, 268, 271, 274, 278, 287, 298, 299, 301, 302, 306, 303

(56) References Cited

U.S. PATENT DOCUMENTS 5,523,520 A * 6/1996 Hunsperger et al. ........ 435/410

OTHER PUBLICATIONS

Bennetzen et al. 1992. Approaches and progress in the molecular cloning of plant disease resistance genes. Genetic Engineering 14:99–124.*

Cheung et al. 1997. Conservation of S–locus for self incompatibility in *Brassica napus* (L.) and *Brassica oleracea* (L.). Theor. Appl. Genet. 95:73–82.*

Earle et al. 1994. Cold–tolerant Ogura CMS *Brassica* vegetables for horticultural use. Cruciferae Newsletter 16:80–81.*

Eshed et al. 1996. Less–than–additive epistatic interactions of quantitative trait loci in tomato. Genetics 143:1807–1817.*

Kao et al. 1990. Efficient plant regeneration from hypocotyl protoplasts of broccoli (*Brassica oleracea* L. ssp. italica Plenck). Plant Cell Reports 9:311–315.*

Kott et al. 1990. The role of biotechnology in canola/rapeseed research. Pp. 47–78, in: Rapeseed Production, Nutrition, and Technology. Van Reinold, New York.*

Kraft et al. 2000. Linkage disequilibrium and fingerprinting in sugar beet. Theor. Appl. Genet. 323–326.*

Pang et al. 1992. Expression of a gene encoding scorpion insectotoxin peptide in yeast, bacteria, and plants. Gene 116:165–172.*

* cited by examiner

*Primary Examiner*—David T. Fox
*Assistant Examiner*—Cynthia Collins
(74) *Attorney, Agent, or Firm*—Jondle & Associates PC

(57) ABSTRACT

Inbred broccoli line, designated BRM50-3905 is disclosed. The invention relates to the seeds of inbred broccoli line BRM50-3905, to the plants of inbred broccoli line BRM50-3905, and to methods for producing a broccoli plant produced by crossing the inbred line BRM50-3905 with itself or another broccoli line. The invention further relates to hybrid broccoli seeds and plants produced by crossing the inbred line BRM50-3905 with another broccoli line.

10 Claims, No Drawings

INBRED BROCCOLI LINE BRM50-3905

BACKGROUND OF THE INVENTION

This invention relates to new and distinctive broccoli inbred line, designated BRM50-3905. There are numerous steps involved in the development of any new and novel desirable germplasm with superior combining ability. Plant breeding begins with the analysis and definition of problems and weaknesses of the current germplasm, the establishment of program goals, and definition of specific breeding objectives. The next step is selection of germplasm that posses the traits to meet the program goals and the best breeding method to reach those goals. The objective is to combine in a single variety or hybrid an improved combination of desirable traits from the parental germplasm. These important characteristics may include higher yield, better flavor, improved color and field holding ability, resistance to diseases and insects along with economic seed yields to facilitate the cost of hybrid seed production.

The method chosen for breeding or selection depends on the mode of plant reproduction, the heritability of the trait(s) being improved, and the cultivar (variety) used commercially (e.g. $F_1$ hybrid, pureline). The complexity of inheritance influences choice of breeding method. A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, observation in multiple locations and seasons provide a better estimate of its genetic worth.

The development of commercial broccoli hybrids requires the development of homozygous inbred lines. Breeding programs combine desirable traits from two or more germplasm sources from which various broad based breeding gene pools are used to develop inbred lines by selfing followed by selection of desired phenotypes sometimes utilizing anther, microspore and ovule culture to speed up and improve selection efficiency.

The goal of plant breeding is to develop new, unique, and superior broccoli cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same broccoli traits.

Description of breeding methods that are commonly used for different traits and crops can be found in one of several reference books. (e.g. Allard, R. W. "Principles of Plant Breeding" John Wiley and Son, pp. 115–161, 1960; Simmonds, 1979; Sneep et al., 1979; Fehr, 1987).

Proper testing and evaluation should detect any major faults and establish the level of superiority or improvement over current cultivars. In addition to showing superior performance, there must be a demand for a new cultivar that is compatible with industry standards or which creates a new market. For seed-propagated cultivars, it must be feasible to maintain the inbred lines and produce seed easily and economically.

Broccoli, *Brassica oleracea* L., is a new crop in North, South and Central America, Europe and Asia. The introduction of hybrid cultivars in the 1960's provided a magnitude increase in yield, holding ability, expanded growing seasons and large scale production of broccoli. The goal in broccoli breeding is to make continued improvement in hybrid broccoli yields and horticultural characteristics in order to sustain the supply to meet continuous increase in demand for broccoli in developed and emerging world economies. To accomplish this goal new breeding methods such as anther culture and microspore culture have been utilized to more rapidly generate inbred broccoli lines from more diverse germplasm sources.

Broccoli (*Brassica oleracea*, L.) belongs to the mustard family. All *Brassica oleracea* will cross pollinate. Pollination is effected by insect vectors, most common of which is the honey bee. Broccoli, like most other Brassica, have a genetic characteristic of self incompatibility which encourages cross pollination resulting in higher levels of variability. Variability in populations is desired for wide adaptation and survival. Broccoli breeding populations can be inbred or backcrossed for 8 to 9 generations and/or with the use of double haploids derived from anther culture to develop homozygous inbred lines. Broccoli $F_1$ hybrids can be produced by using self-incompatibility or cytoplasmic male sterility to control pollen movement between selected inbred lines.

Self-incompatibility is a breeding system that enforces outcrossing and therefore maximizes recombination in cross pollinated species. This breeding system in nature has been utilized by man in $F_1$ hybrid breeding, especially in Brassica vegetables (Tsunoda et al., chapter 13).

Cytoplasmic male sterility (CMS) is another method used in Brassica vegetables species to produce $F_1$ hybrids. This method of producing hybrids in Brassica is a more recent development compared to self-incompatibility. A genetic mutation contained in the cytoplasm (mitochondria) is responsible for the lack of production of pollen. In Brassica, the cytoplasm has commonly been identified in and transferred from "Ogura"-type radish (Ogura, 1968). The major advantage of CMS over self-incompatibility is that under normal conditions, no pollen is produced in the female parent. This results in the production of 100% hybrid seed. Under certain stressful growth conditions, however, it may be possible to produce small amounts of fertile pollen in CMS plants. Brassica inbreds containing CMS are maintained by continued hybridization to their normal (fertile) counterpart inbred, commonly referred to as a "B" line.

The plants associated with the Brassica group have been familiar to mankind since ancient times, and always of great agricultural importance. Brassica is a major food species worldwide. Brassica species have a general adaptation for cool climate growing conditions. Therefore, adaptation has occurred for summer growing conditions with cool to moderate climates and for winter growing conditions in warmer or tropical locations.

SUMMARY OF THE INVENTION

The invention comprises a novel inbred broccoli line, designated BRM50-3905. This invention thus relates to the seeds of inbred broccoli line BRM50-3905, to the plants of inbred broccoli line BRM50-3905, to methods used for controlling pollination when making hybrid seed with BRM50-3905, and to methods for producing a broccoli plant by crossing the inbred broccoli line BRM50-3905 with itself or another broccoli line. This invention further relates to hybrid broccoli seeds and plants produced by crossing the inbred line BRM50-3905 with another broccoli line.

The invention also comprises a novel inbred broccoli line, designated BRM50-3906. This invention thus relates to the seeds of inbred broccoli line BRM50-3906, to the plants of inbred broccoli line BRM50-3906, to methods used for controlling pollination when making hybrid seed with BRM50-3906, and to methods for producing a broccoli plant by crossing the inbred broccoli line BRM50-3906 with itself or another broccoli line. This invention further relates to hybrid broccoli seeds and plants produced by crossing the inbred line BRM50-3906 with another broccoli line.

DETAILED DESCRIPTION OF THE NEW PLANT

Definitions

In the description and tables which follow, a number of terms are used. In order to provide a clear and consistent understanding of the specification and claims, including the scope to be given such terms, the following definitions are provided.

Average Weight: The average weight is the average weight for an entire plot of harvested broccoli head.

Overall Rating Score: This Overall Rating Score is rated on a scale of 1 to 5. A score of 5 indicated an excellent overall rating. A score of 3.0 indicates average, and a score of 1 indicates poor.

Color: Color means the color of the head at maturity.

Disease and Insect Ratings: Disease and Insects are rated on a scale of 1 to 5. A score of 5 indicates severe damage. A score of 3.0 indicates moderate damage, and a score of 1 indicates no damage.

Inbred broccoli (*Brassica oleracea* L.) BRM50-3905 and BRM50-3906 have superior characteristics, and provide an excellent parental line in crosses for producing first generation ($F_1$) hybrid broccoli. The $F_1$ hybrids with BRM50-3905 and BRM50-3906 have a high tolerance to bacterial soft rot which is very important in areas with high rainfall and humidity like northwestern Europe and which results in higher returns to the grower and improved shelf life. The $F_1$ hybrids with BRM50-3905 and BRM50-3906 have a high tolerance to hollow stem which is important in areas with lower planting densities and/or fast growth which results in improved shelf life and higher returns to the grower. The $F_1$ hybrids with BRM50-3905 and BRM50-3906 have a high tolerance to 'cateyes' which result in a more attractive product with uniform bead. The $F_1$ hybrids of the instant invention produce a more compact and solid head which result in higher weight per head and head diameter as compared to commercial hybrids, Marathon, Legacy and Decathlon which in turn increases yield for the grower and provides a better product for processing since the outer florets do not crumble. BRM50-3905 and BRM50-3906 produce a more 'open' plant type, narrower leaf petioles and smaller scars on the stem which makes the product easier to harvest and clean, decreasing labor costs and increasing returns to the grower. The longer field standing ability of BRM50-3905 and BRM50-3906 provides greater flexibility to the grower. With the combination of all of these improved traits, the yield is increased over the leading commercial broccoli varieties Marathon, Legacy and Decathlon.

The inbred has shown uniformity and stability for all traits, as described in the following variety description information. The line has been increased and maintained by pollination with fertile inbred line GIX with continued observation for uniformity.

The inbred broccoli line BRM50-3905 has the following morphologic and other characteristics.

Variety Description Information

MATURITY: Late

PLANT CHARACTERISTICS:

No. of Stems: 1

Head Color: Blue-green

Plant Height: Tall

A cytoplasmic male sterility gene was backcrossed into BRM50-3905 to produce BMR50-3906. BMR50-3906 is maintained by cross pollination with a fertile maintainer line which is maintained by self-pollination. BMR50-3906 has the following characteristics:

MATURITY: Late

PLANT CHARACTERISTICS:

No. of Stems: 1

Head Color: Blue-green

Plant Height: Tall

This invention is also directed to methods for producing a broccoli by crossing a first parent broccoli plant with a second parent broccoli plant, wherein the first or second broccoli plant is the inbred broccoli from the line BRM50-3905 or BRM50-3906. Further, both first and second parent broccoli plants may be from the inbred line BRM50-3905 or BRM50-3906. Therefore, any methods using the inbred broccoli line BRM50-3905 or BRM50-3906 are part of this invention; selfing, backcrosses, hybrid breeding, and crosses to populations. Any plants produced using inbred broccoli line BRM50-3905 or BRM50-3906 as a parent are within the scope of this invention. Advantageously, the inbred broccoli line is used in crosses with other broccoli varieties to produce first generation ($F_1$) broccoli hybrid seed and plants with superior characteristics.

As used herein, the term "plant" includes plant cells, plant protoplasts, plant cells of tissue culture from which broccoli plants can be regenerated, plant calli, plant clumps, and plant cells that are intact in plants or parts of plants, such as pollen, flowers, seeds, stalks, stumps, leaves and the like. Thus, another aspect of this invention is to provide for cells which upon growth and differentiation produce the inbred broccoli BRM50-3905 or BRM50-3906.

Table

In Table 1 that follows, the traits and characteristics of the hybrid RS1140 which has BRM50-3905 as one of its parents, are given in comparison with other commercial broccoli varieties.

As shown in the Table, RS1140 which is the variety which has BRM50-3905 as one of its parents clearly outperforms the other commercial varieties, Marathon, Decathlon and Legacy in most categories.

| | | | | Broccoli Trait Comparison United Kingdom - 1999 Plant Date: July 20 | | | | | |
|---|---|---|---|---|---|---|---|---|---|
| Name | 50% Mat. | Avg Wt | Unif | Plant Type | Head Type | Bead Size | Stem Quality | Overall | Disease |
| RS1140 | Oct 15 | 500 | 4.5 | 4.5 | 4.5 | 4.5 | 4.5 | 4.5 | 4.0 |
| Marathon | Oct 13 | 480 | 2.0 | 4.0 | 3.0 | 4.0 | 3.0 | 3.0 | 4.0 |
| Decathlon | Oct 6 | 350 | 3.5 | 4.5 | 3.0 | 4.0 | 4.0 | 3.0 | 4.5 |

| | | | | Broccoli Trait Comparison United Kingdom - 2000 Plant Date: July 5 | | | | | |
|---|---|---|---|---|---|---|---|---|---|
| Name | 50% Mat. | Avg Wt | Unif | Plant Type | Head Type | Bead Size | Stem Quality | Overall | Disease |
| RS1140 | Sep 19 | 670* | 3.0 | 5.0 | 5.0 | 3.5 | 4.5 | 4.5 | 3.5 |
| Marathon | Sep 13 | 600 | 3.0 | 3.0 | 2.5 | 4.0 | — | 2.5 | 3.5 |
| Legacy | Sep 13 | 620 | 2.5 | 3.5 | 3.0 | 4.0 | — | 3.0 | 3.5 |

*Due to an unusually poor seed lot this number has been recalculated.

Deposit Information

A deposit of the Seminis Vegetable Seeds propietary inbred broccoli line BRM50-3905 disclosed above and recited in the appended claims has been made with the American Type Culture Collection (ATCC), 10801 University Boulevard, Manassas, Virgina 20110. The date of deposit was May 15, 2003. The deposit of 2,500 seeds were taken from the same deposit maintained by Seminis Vegetable Seeds since prior to the filling date of this application. All restrictions upon the deposit have been removed, and the deposit is intended to meet all of the requirements of 37 C.F.R. §1.801–1.809. The ATCC accession number is PTA-5198. The deposit will be maintained in the depository for a period of 30 years, or 5 years after the last request, or for the effective life of the patent, whichever is longer, and will be replaced as necessary during that period.

What is claimed is:

1. An inbred broccoli seed designated BRM50-3905, a sample of said seed having been deposited under ATCC Accession No. PTA5198.

2. A broccoli plant, or parts thereof, produced by growing the seed of claim 1.

3. Pollen of the plant of claim 2.

4. An ovule of the plant of claim 2.

5. A broccoli plant, or parts thereof, having all of the physiological and morphological characteristics of the broccoli plant of claim 2.

6. A tissue culture of regenerable cells of a broccoli plant of inbred line BRM50-3905, wherein the tissue regenerates plants capable of expressing all the morphological and physiological characteristics of the inbred line BRM50-3905.

7. A tissue culture according to claim 6, the cells or protoplasts being from a tissue selected from the group consisting of leaves, pollen, embryos, roots, root tips, anthers, flowers, fruit, and seeds.

8. A method for producing a hybrid broccoli seed comprising crossing a first inbred parent broccoli plant with a second parent broccoli plant and harvesting the resultant hybrid broccoli seed, wherein said first or second parent broccoli plant is the broccoli plant of claim 2.

9. A method of making a male sterile broccoli plant, said method comprising transforming the broccoli plant of claim 2 with a gene conferring male sterility.

10. The male sterile broccoli plant produced by the method of claim 9.

* * * * *